United States Patent
Chang et al.

(10) Patent No.: US 10,041,962 B1
(45) Date of Patent: Aug. 7, 2018

(54) SENSING PAPER AND METHOD OF SENSING ABUSED DRUGS

(71) Applicant: National Taiwan University, Taipei (TW)

(72) Inventors: Huan-Tsung Chang, Taipei (TW); Yao-Te Yen, Taipei (TW); Yu-Syuan Lin, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 15/861,675

(22) Filed: Jan. 4, 2018

(30) Foreign Application Priority Data

Sep. 28, 2017 (TW) .............................. 106133253 A

(51) Int. Cl.
*G01N 21/64* (2006.01)
*G01N 33/94* (2006.01)
*B32B 29/00* (2006.01)

(52) U.S. Cl.
CPC ............. *G01N 33/94* (2013.01); *G01N 21/64* (2013.01); *B32B 29/002* (2013.01)

(58) Field of Classification Search
CPC ....... B32B 29/002; G01N 21/64; G01N 33/94
See application file for complete search history.

(56) References Cited

U.S. PATENT DOCUMENTS

| | | |
|---|---|---|
| 8,319,194 B2 | 11/2012 | Hashimoto et al. |
| 9,128,108 B2 | 9/2015 | McConnell et al. |
| 9,347,961 B2 | 5/2016 | Karlsen et al. |
| 2011/0039346 A1 | 2/2011 | Bradley et al. |
| 2011/0050431 A1 | 3/2011 | Hood et al. |
| 2012/0329168 A1 | 12/2012 | Lin et al. |
| 2014/0043488 A1 | 2/2014 | Treado et al. |
| 2014/0193840 A1* | 7/2014 | Hsu ................ G01N 33/548 435/7.92 |
| 2016/0016166 A1* | 1/2016 | Rolland ........... B01L 3/502707 506/9 |

(Continued)

FOREIGN PATENT DOCUMENTS

| CN | 203551563 | 4/2014 |
|---|---|---|
| CN | 104458693 | 3/2015 |

(Continued)

OTHER PUBLICATIONS

Maria Pilar Chantada-Vazquez, et al., "Simple and Sensitive Molecularly Imprinted Polymer—Mn-Doped ZnS Quantum Dots Based Fluorescence Probe for Cocaine and Metabolites Determination in Urine," Anal. Chem, vol. 88, Feb. 2016, pp. 2734-2741.

*Primary Examiner* — Mark R Gaworecki
(74) *Attorney, Agent, or Firm* — JCIPRNET

(57) ABSTRACT

A sensing paper suitable for sensing a target substance is provided. The sensing paper includes a filter paper, a wax, and a plurality of fluorescent materials. The wax is printed on the filter paper, wherein the sensing paper has a plurality of opening patterns, and each of the opening patterns respectively exposes a portion of the filter paper. The plurality of fluorescent materials is attached to the portion of the filter paper that is exposed by each of the opening patterns. Each of the fluorescent materials emits fluorescence, and after the fluorescent materials react with the target substance, an intensity of the fluorescence emitted by the fluorescent materials is quenched.

12 Claims, 7 Drawing Sheets

(56) References Cited

U.S. PATENT DOCUMENTS

2016/0116427 A1* 4/2016 Laurenson ........... G01N 27/327
                                                                  422/82.01
2016/0376631 A1* 12/2016 Liang ....................... C12Q 1/32
                                                                       435/26
2017/0315078 A1* 11/2017 Laurenson ........... G01N 27/327

FOREIGN PATENT DOCUMENTS

| | | |
|---|---|---|
| CN | 104568890 | 4/2015 |
| CN | 104570135 | 4/2015 |
| CN | 204287194 | 4/2015 |
| CN | 205027758 | 2/2016 |
| EP | 2300831 | 12/2013 |
| EP | 2361387 | 4/2014 |
| EP | 3002592 | 4/2016 |
| TW | M425275 | 3/2012 |
| TW | I571634 | 2/2017 |

* cited by examiner

SENSING PAPER AND METHOD OF SENSING ABUSED DRUGS

CROSS-REFERENCE TO RELATED APPLICATION

This application claims the priority benefit of Taiwan application serial no. 106133253, filed on Sep. 28, 2017. The entirety of the above-mentioned patent application is hereby incorporated by reference herein and made a part of this specification.

BACKGROUND OF THE INVENTION

Field of the Invention

The invention relates to a sensing paper, and in particular, to a sensing paper for sensing abused drugs and a method of sensing abused drugs by using the sensing paper.

Description of Related Art

The fabrication principle of the commercially available sensing papers/agents currently used for abused drug quick screening is mostly based on the immunological method, in which after abused drug molecules react with antibodies on a sensing paper/agent, the antibodies may release dye molecules, which produce colorings that may be detected. Although the sensing paper/agent using the immunological method exhibits the advantage of high specificity, the abused drug quick screening using the immunological method still has its disadvantages. For example, the antibodies on the sensing paper/agent need to be obtained through animal experiments, so this method is less humane. Moreover, the physiological states of each batch of animals all affect the quality of the antibodies, and the generated antibodies thus differ among the different batches. In addition, when sensing is performed, at least 1 mL of the specimen liquid needs to be dripped for reaction or elution. In other words, the commercially available sensing papers/agents currently used for abused drug quick screening have many disadvantages including difficulty in production of antibodies, high costs, short shelf-life, and difficulty in storage. In light of the above, a sensing paper and a sensing method capable of addressing the foregoing issues are urgently needed.

SUMMARY OF THE INVENTION

The invention provides a sensing paper and a method of sensing abused drugs that exhibit the advantages of manufacturing simplicity, low costs, and ease of storage.

A sensing paper of the invention is suitable for sensing a target substance (abused drug). The sensing paper includes a filter paper, a wax, and a plurality of fluorescent materials. The wax is printed on the filter paper, wherein the wax has a plurality of opening patterns, and each of the opening patterns respectively exposes a portion of the filter paper. The plurality of fluorescent materials is attached to the portion of the filter paper that is exposed by each of the opening patterns. Each of the fluorescent materials emits fluorescence, and after the fluorescent materials react with the target substance, an intensity of the fluorescence emitted by the fluorescent materials is quenched.

In an embodiment of the invention, the opening patterns are circular opening patterns, and the circular opening patterns are disposed separate from each other.

In an embodiment of the invention, the wax is printed on a first surface and a second surface opposite to the first surface of the filter paper, and the wax on the first surface has the opening patterns and the wax on the second surface does not have the opening patterns.

In an embodiment of the invention, the fluorescent materials are carbon quantum dots, and a size of the carbon quantum dots respectively ranges from 2.77 nm to 6.14 nm.

In an embodiment of the invention, a highest occupied molecular orbital (HOMO) of the carbon quantum dots is −4.51 eV, and a lowest unoccupied molecular orbital (LUMO) of the carbon quantum dots is −1.48 eV.

In an embodiment of the invention, a lowest unoccupied molecular orbital (LUMO) of the target substance (abused drug) to be sensed is lower than a lowest unoccupied molecular orbital (LUMO) of the fluorescent materials, so that the fluorescent materials undergo electron transfer and cause the intensity of the fluorescence emitted by the fluorescent materials to be quenched.

In an embodiment of the invention, the fluorescent materials emit blue fluorescence after being excited by ultraviolet light, and after the fluorescent materials react with the target substance, an intensity of the blue fluorescence emitted by the fluorescent materials is quenched.

In an embodiment of the invention, the target substance is cocaine or cathinone.

A method of sensing abused drugs of the invention includes the following steps: providing the sensing paper, and dripping a sensing liquid into at least one of the opening patterns of the sensing paper; performing irradiation with an ultraviolet light source after the sensing liquid reacts with the fluorescent materials in the opening pattern; and under the irradiation of the ultraviolet light source, determine a quenching rate of the intensity of the fluorescence of the fluorescent materials in the opening pattern so as to verify the presence of an abused drug in the sensing liquid, and verifying a concentration of the abused drug in the sensing liquid according to the quenching rate.

In an embodiment of the invention, 10 μL of the sensing liquid is dripped into the at least one of the opening patterns of the sensing paper for reaction.

In an embodiment of the invention, after the sensing liquid reacts with the fluorescent materials in the opening pattern, a solvent of the sensing liquid is evaporated and then the irradiation is performed with the ultraviolet light source.

In an embodiment of the invention, a method of verifying the concentration of the abused drug in the sensing liquid according to the quenching rate includes: providing a series of the abused drug at known concentrations in the opening patterns of the sensing paper; performing irradiation with the ultraviolet light source after the abused drug reacts with the fluorescent materials in the opening patterns; determining fluorescent intensities with the abused drug at each concentration to plot a standard concentration versus relative fluorescence quenching rate curve; and determining the quenching rate based on the standard concentration versus relative fluorescence quenching rate curve to verify the concentration of the abused drug in the sensing liquid.

In light of the above, as the sensing paper of the invention is attached with the fluorescent materials, when the fluorescent materials react with molecules of the abused drug, the fluorescence of the fluorescent materials is rapidly quenched, and the concentration of the abused drug can be quantified based on the quenching rate. By using the fluorescent materials as the sensing substances, the sensing paper of the invention exhibits advantages including high stability, stability to heat and humidity, resistance to deterioration, and ease of storage. Moreover, quality control of the chemically synthesized fluorescent materials may be monitored, such that high stability is secured among batches of products. In addition, the fluorescent materials of the invention may be synthesized from organic materials, and even organic waste materials can all be used as synthesis precursors of the invention, which is in line with the concept of green chemistry. In other words, the sensing paper of the invention exhibits advantages of manufacturing simplicity, low costs, and ease of storage and is suitable for sensing a variety of abused drugs.

To provide a further understanding of the aforementioned and other features and advantages of the disclosure, exemplary embodiments, together with the reference drawings, are described in detail below.

DESCRIPTION OF THE EMBODIMENTS

Figure 1:
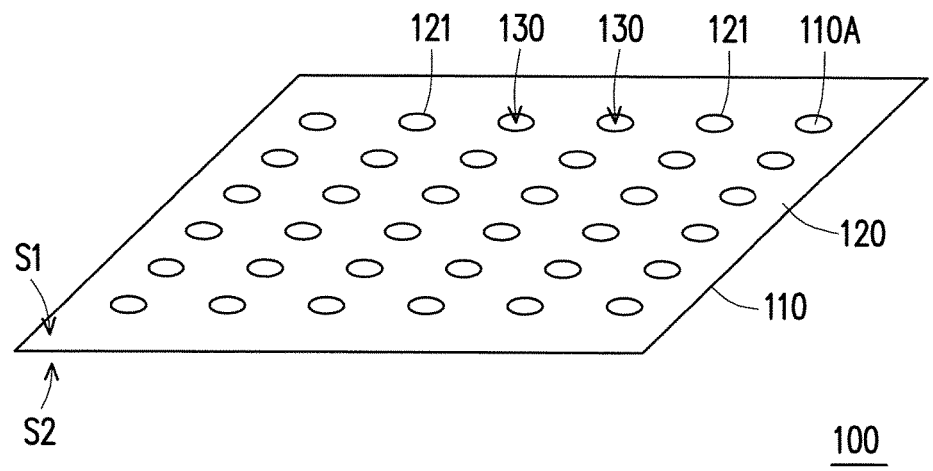
FIG. 1 is a schematic diagram illustrating a top view of a sensing paper according to an embodiment of the invention.

FIG. 1 is a schematic diagram illustrating a top view of a sensing paper according to an embodiment of the invention. Referring to FIG. 1, a sensing paper 100 of the present embodiment is suitable for sensing a specific target substance. The target substance is, for example, any of various abused drugs including cocaine and cathinone. The sensing paper 100 includes a filter paper 110, a wax 120, and a plurality of fluorescent materials 130. As shown in FIG. 1, the wax 120 is printed on the filter paper 110, wherein the wax 120 of the sensing paper 100 has a plurality of opening patterns 121, and each of the opening patterns 121 exposes a portion 110A of the filter paper 110. In the present embodiment, the wax 120 is, for example, printed on a first surface S1 and a second surface S2 opposite to the first surface S1 of the filter paper 110. Moreover, the wax 120 on the first surface S has the opening patterns 121, and the wax 120 on the second surface S2 does not have the opening patterns 121. The opening patterns 121 are, for example, circular opening patterns, and the circular opening patterns are disposed separate from each other, but the invention is not limited thereto. In other embodiments, the opening patterns 121 may also be opening patterns 121 in other shapes, which may be adjusted according to requirement. Moreover, in the present embodiment, a diameter of each of the circular opening patterns is, for example, 5 mm, and a number of the circular opening patterns is, for example, 36, but the invention is not limited thereto. In other embodiments, the number and the diameter of the circular opening patterns may also be adjusted according to requirement.

Specifically, the wax 120 is printed on the filter paper 110 by using the solid-ink printing method, for example. In the solid-ink printing method, a wax printer (Xerox 8570) prints a plurality of circular opening patterns on one of the surfaces of the filter paper 110 and prints the wax 120 on the other surface of the filter paper 110. Then, the filter paper 110 printed with the wax 120 is placed on a heating plate and heated at 140° C. for 1 minute to allow the wax 120 to penetrate the filter paper 110 and form a hydrophobic layer. By using this method, a plurality of channels/openings are formed on the filter paper 110, so that the filter paper 110 can carry the fluorescent materials 130 for sensing the target substance.

In the embodiment of FIG. 1, the plurality of fluorescent materials 130 are attached to the portion 110A of the filter paper 110 that is exposed by the opening patterns 121, and the fluorescent materials 130 emit fluorescence. A method of attaching the fluorescent materials 130 to the opening patterns 121 includes, for example, dripping an adequate amount (4 μL) of the fluorescent materials 130 into the portion 110A of the filter paper 110 exposed by each of the opening patterns 121, and evaporating excessive liquid/solvent at a temperature of 50° C. In the present embodiment, the fluorescent materials 130 are, for example, carbon quantum dots, and a size of the carbon quantum dots respectively ranges from 2.77 nm to 6.14 nm, but the invention is not limited thereto. In other embodiments, the fluorescent materials 130 may be any substances that emit fluorescence. However, it shall be noted that, in order to effectively sense the target substance (abused drug), a lowest unoccupied molecular orbital (LUMO) of the target substance shall be lower than a lowest unoccupied molecular orbital (LUMO) of the fluorescent materials 130, so that the fluorescent materials 130 can undergo electron transfer and cause an intensity of the fluorescence emitted by the fluorescent materials 130 to be quenched. In other words, after the fluorescent materials 130 react with the target substance (abused drug), the intensity of the fluorescence emitted by the fluorescent materials 130 is quenched, and thereby the presence of the target substance can be determined.

For example, the fluorescent materials 130 of an embodiment of the invention are carbon quantum dots, and a highest occupied molecular orbital (HOMO) of the carbon quantum dots is −4.51 eV, and a lowest unoccupied molecular orbital (LUMO) of the carbon quantum dots is −1.48 eV. Therefore, the target substance needs to have a lowest unoccupied molecular orbital (LUMO) lower than −1.48 eV so as to be sensed. Accordingly, different target substances (abused drugs) may be sensed by selecting the adequate fluorescent materials 130. In the present embodiment, the carbon quantum dots being the fluorescent materials 130 are at least suitable for sensing abused drugs including cocaine and cathinone. When the fluorescent materials 130 are carbon quantum dots, the fluorescent materials 130 emit blue fluorescence after being excited by ultraviolet light, and after the fluorescent materials 130 react with the target substance, an intensity of the blue fluorescence emitted by the fluorescent materials 130 is quenched, and thereby the presence of the abused drug can be determined. Next, a method of sensing abused drugs by using the sensing paper 100 is described below.

Figure 2A:
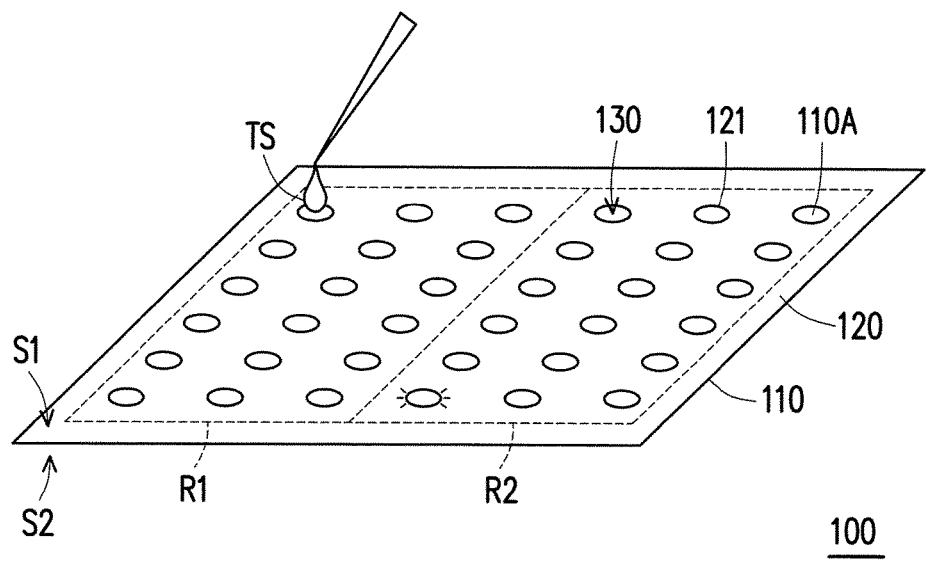
FIG. 2A to FIG. 2B are schematic diagrams illustrating a process of sensing abused drugs by using a sensing paper according to an embodiment of the invention.
Figure 2B:
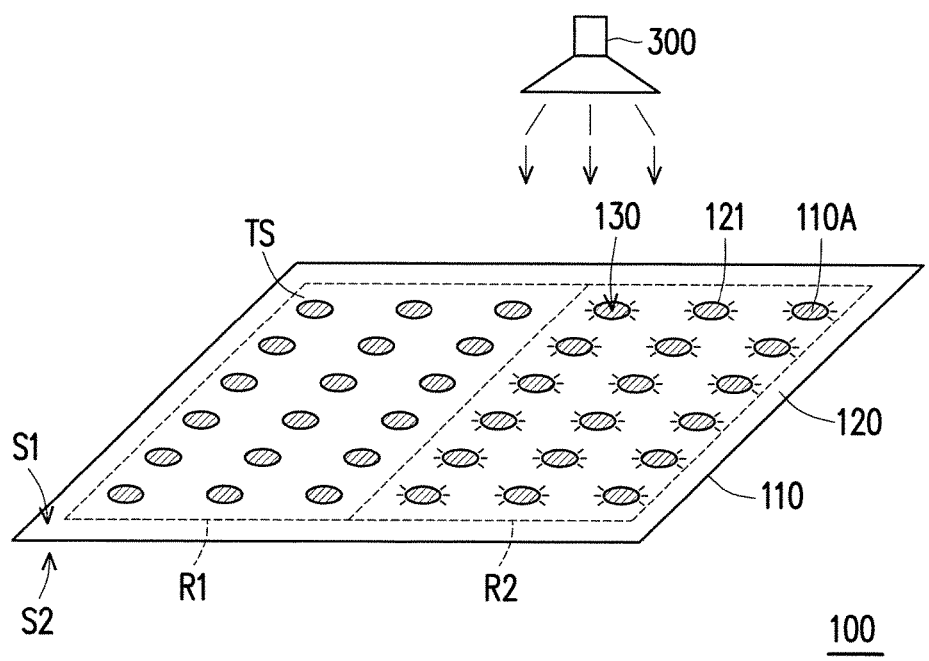

FIG. 2A to FIG. 2B are schematic diagrams illustrating a process of sensing abused drugs by using a sensing paper according to an embodiment of the invention. Referring to FIG. 2A, the sensing paper 100 as shown in FIG. 1 is provided. Subsequently, a sensing liquid TS is dripped into the opening patterns 121 of the sensing paper 100 to allow the sensing liquid TS to react with the fluorescent materials 130 in the opening pattern 121. In the present embodiment, the sensing liquid TS is dripped, for example, into the opening patterns 121 located in a first region R1 of the sensing paper 100, and the opening patterns in a second region R2 do not contain the sensing liquid TS. More specifically, when the opening patterns 121 are circular opening patterns with a diameter of 5 mm, about 10 µL of the sensing liquid TS is dripped into the opening patterns 121 of the sensing paper 100 for reaction.

Next, referring to FIG. 2B, after the sensing liquid TS reacts with the fluorescent materials 130 in the opening patterns 121, irradiation is performed with an ultraviolet light source 300. More specifically, after the sensing liquid TS reacts with the fluorescent materials 130 in the opening patterns 121, the solvent of the sensing liquid TS is evaporated, and then irradiation is performed with the ultraviolet light source 300. With the irradiation of the ultraviolet light source 300, a quenching rate of the fluorescence intensity of the fluorescent materials 130 in the opening patterns 121 at the first region R1 where the sensing liquid TS is dripped is determined to verify the presence of an abused drug in the sensing liquid TS, and further, a concentration of the abused drug in the sensing liquid TS is verified according to the quenching rate. Moreover, the fluorescent materials 130 in the opening patterns 121 at the second region R2 where the sensing liquid TS is not dripped may serve as a control group, which can be used to compare with the fluorescence intensity of the opening patterns 121 in the first region R1 to see if there are obvious differences. When the fluorescence intensities in the first region R1 and the second region R2 are significantly different, these results may be used as a preliminary determination that the sensing liquid TS contains the abused drug.

In the present embodiment, a method of verifying the concentration of the abused drug in the sensing liquid TS according to the quenching rate is described below. First, a series of the abused drug at known concentrations are provided in the opening patterns 121 of the sensing paper 100. After the abused drug reacts with the fluorescent materials 130 in the opening patterns 121, irradiation is performed with the ultraviolet light source 300. Fluorescence intensities of the abused drug at each concentration are determined to plot a standard concentration versus relative fluorescence quenching rate curve. The quenching rate is determined based on the standard concentration versus relative fluorescence quenching rate curve, which helps to verify the concentration of the abused drug in the sensing liquid TS. By using this method, the concentration of the abused drug can be quantified based on the quenching rate of the fluorescence.

EXPERIMENTAL EXAMPLES

To provide a further understanding of the method of sensing abused drugs by using the sensing paper 100 of the invention, experimental examples are provided below for illustration.

Experimental Example A

In the present experimental example, the carbon quantum dots are used as the fluorescent materials 130, and the abused drug to be sensed is 4-Chloroethcathinone. The present experimental example verifies the effect caused by 4-Chloroethcathinone on the fluorescence intensity of the carbon quantum dots in solution. In the present experimental example, a preparation method of the carbon quantum dots includes placing 1.0 g of L-arginine of 99% purity in a Teflon reaction tube containing 20 mL of deionized water for reaction in a microwave digestion oven at 220° C. for 20 minutes. After cooling down the reacted liquid, a dark brown liquid is obtained. The dark brown liquid is purified through a dialysis method to obtain pure carbon quantum dots. Next, 40 µL of the obtained pure carbon quantum dots are added into sodium phosphate buffers with different concentrations of 4-Chloroethcathinone (0 to 25 mM) for reaction for 1 minute and are irradiated with ultraviolet light at 365 nm to verify their fluorescence emission spectra. The experimental result is shown in FIG. 3.

Figure 3:
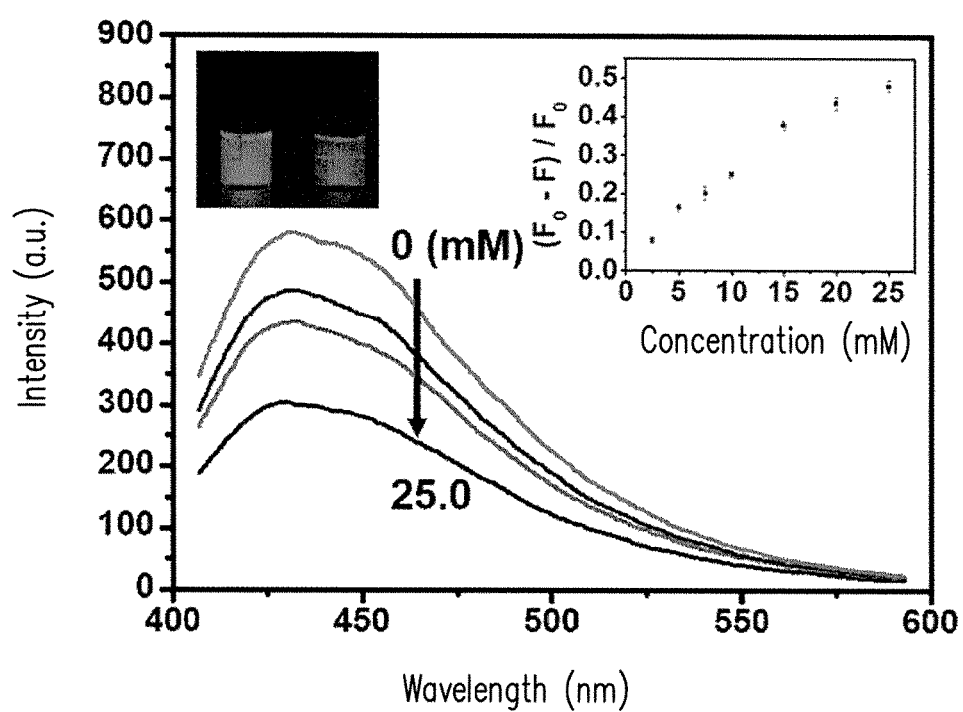
FIG. 3 illustrates fluorescence emission spectra of carbon quantum dots mixed with 4-Chloroethcathinone of different concentrations according to an embodiment of the invention.

FIG. 3 illustrates fluorescence emission spectra of carbon quantum dots mixed with 4-Chloroethcathinone of different concentrations according to an embodiment of the invention. As shown in FIG. 3, as the concentration of 4-Chloroethcathinone increases, the fluorescence intensity of the carbon quantum dots decreases. In other words, 4-Chloroethcathinone can cause significant fluorescence quenching of the carbon quantum dots. Moreover, as shown in FIG. 3, a relative fluorescence quenching rate $(F_0-F)/F_0$ (F and $F_0$ are values of fluorescence intensities of the carbon quantum dots in the presence and absence of 4-Chloroethcathinone) of the carbon quantum dots has a linear relationship with the standard concentration of 4-Chloroethcathinone. In other words, the amount of 4-Chloroethcathinone and the quenching rate of the carbon quantum dots are positively correlated. Through the foregoing experiment, it is verified that 4-Chloroethcathinone affects the fluorescence intensity of the carbon quantum dots to a certain degree. Therefore, the carbon quantum dots may be used as the fluorescent materials 130 in the sensing paper 100 of the invention to sense the presence of 4-Chloroethcathinone.

Experimental Example B

In the present experimental example, values of relative fluorescence quenching rates of the carbon quantum dots mixed with different abused drugs and dopants are sensed to verify the quenching effect. First, abused drugs, including ephedrine, ketamine, methamphetamine, heroin, cocaine, and 4-Chloroethcathinone, and possible interfering substances, including glucose, sucrose, and fructose, are tested and respectively dissolved in a phosphate buffer (pH 7.0 or pH 11.0; 100 mM). Subsequently, the solutions are respectively dripped into the sensing paper attached with the carbon quantum dots and are sensed under irradiation of ultraviolet light. Next, the relative fluorescence quenching rates $(F_0-F)/F_0$ of the carbon quantum dots are calculated according to the sensed fluorescence intensities, and the experimental results are shown in FIG. 4A and FIG. 4B.

Figure 4A:
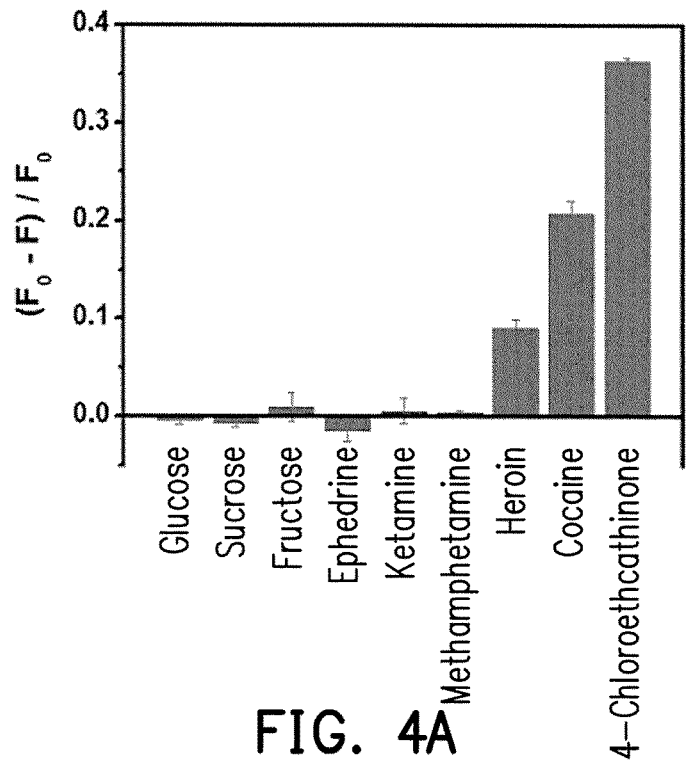
FIG. 4A is a graph illustrating values of relative fluorescence quenching rates of carbon quantum dots mixed with different abused drugs and dopants in a neutral solution.
Figure 4B:
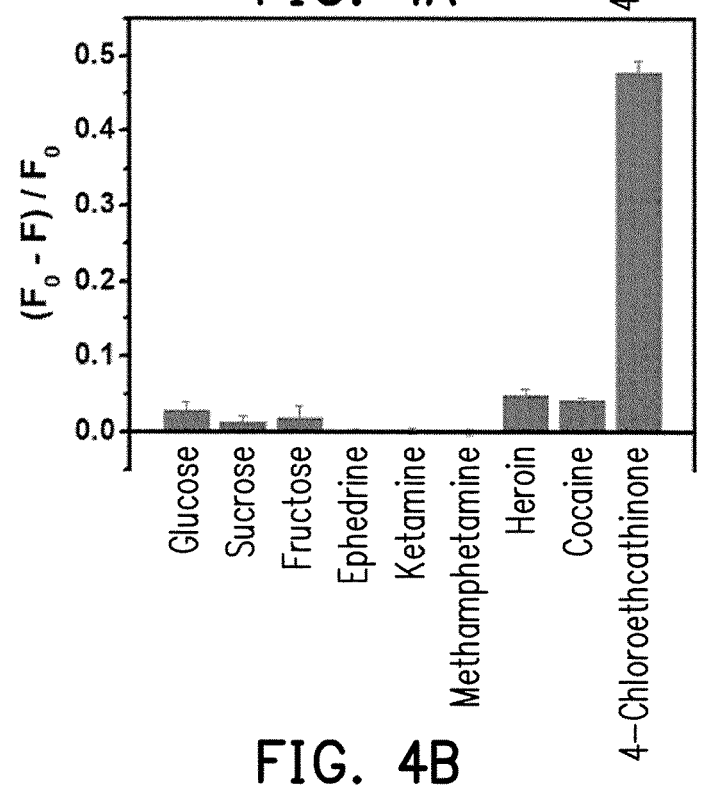
FIG. 4B is a graph illustrating values of relative fluorescence quenching rates of carbon quantum dots mixed with different abused drugs and dopants in an alkaline solution.

FIG. 4A is a graph illustrating values of relative fluorescence quenching rates of carbon quantum dots mixed with different abused drugs and dopants in a neutral solution (pH 7.0). Referring to FIG. 4A, it is found that the relative fluorescence quenching rates of cocaine and 4-Chloroethcathinone are the highest. In other words, in the neutral solution, cocaine and 4-Chloroethcathinone can affect the fluorescence intensity of the carbon quantum dots to a certain degree, wherein 4-Chloroethcathinone affects the fluorescence intensity the most. In contrast, ephedrine, ketamine, methamphetamine, glucose, sucrose, and fructose do not seem to affect the fluorescence intensity of the carbon quantum dots. That is, the fluorescence quenching rates are not high. FIG. 4B is a graph illustrating values of relative fluorescence quenching rates of carbon quantum dots mixed with different abused drugs and dopants in an alkaline solution (pH 11.0). Referring to FIG. 4B, it is found that the relative fluorescence quenching rate of 4-Chloroethcathinone is the highest. In other words, 4-Chloroethcathinone affects the fluorescence intensity the most in the alkaline solution. In contrast, heroin, cocaine, ephedrine, ketamine, methamphetamine, glucose, sucrose, and fructose do not seem to affect the fluorescence intensity of the carbon quantum dots. That is, the fluorescence quenching rates are not high. Accordingly, it is found that 4-Chloroethcathinone can cause the fluorescence intensity of the carbon quantum dots to be quenched in both the neutral solution and the alkaline solution, while cocaine can cause the fluorescence intensity of the carbon quantum dots to be quenched in the neutral solution.

Referring to the listed values of the highest occupied molecular orbitals (HOMO) and the lowest unoccupied molecular orbitals (LUMO) of the carbon quantum dots and each of the abused drugs shown in Table 1, it is found that the lowest unoccupied molecular orbitals (LUMO) of cocaine and 4-Chloroethcathinone are both lower than the lowest unoccupied molecular orbital (LUMO) of the carbon quantum dots. Therefore, cocaine and 4-Chloroethcathinone can cause the carbon quantum dots to undergo electron transfer and cause the intensity of the fluorescence emitted by the carbon quantum dots to be quenched. In contrast, the lowest unoccupied molecular orbital (LUMO) of ephedrine is higher than the lowest unoccupied molecular orbital (LUMO) of the carbon quantum dots. As such, ephedrine cannot induce electron transfer and cause the fluorescence intensity to be quenched. Based on this principle, adequate fluorescent materials may be selected for sensing the corresponding abused drugs.

TABLE 1

HOMO and LOMO values of carbon quantum dots and abused drugs

| Sample | HOMO (eV) | LOMO (eV) | Energy gap (eV) |
|---|---|---|---|
| Carbon quantum dots | −4.51 | −1.48 | 3.03 |
| Cocaine | −5.93 | −1.80 | 4.13 |
| 4-Chloroethcathinone | −6.01 | −1.95 | 4.06 |
| Ephedrine | −5.07 | −0.61 | 4.46 |

Experimental Example C

Through Experimental Example A and Experimental Example B above, it is noted that 4-Chloroethcathinone causes the greatest quenching rate to the fluorescence intensity of the carbon quantum dots. Therefore, in the present experimental example, the carbon quantum dots are used as the fluorescent materials 130 on the sensing paper 100, and the fluorescence quenching rates caused by 4-Chloroethcathinone of different concentrations are verified under irradiation of the ultraviolet light source 300 at different wavelengths. Specifically, in the present experimental example, 2.5 mM to 25 mM of 4-Chloroethcathinone is irradiated with the ultraviolet light source at a wavelength of 365 nm to plot a standard concentration of 4-Chloroethcathinone versus the relative fluorescence quenching rate curve. Alternatively, 1.0 mM to 25 mM of 4-Chloroethcathinone is irradiated with the ultraviolet light source at a wavelength of 256 nm to plot a standard concentration of 4-Chloroethcathinone versus the relative fluorescence quenching rate curve. The experimental results are shown in FIG. 5A and FIG. 5B.

Figure 5A:
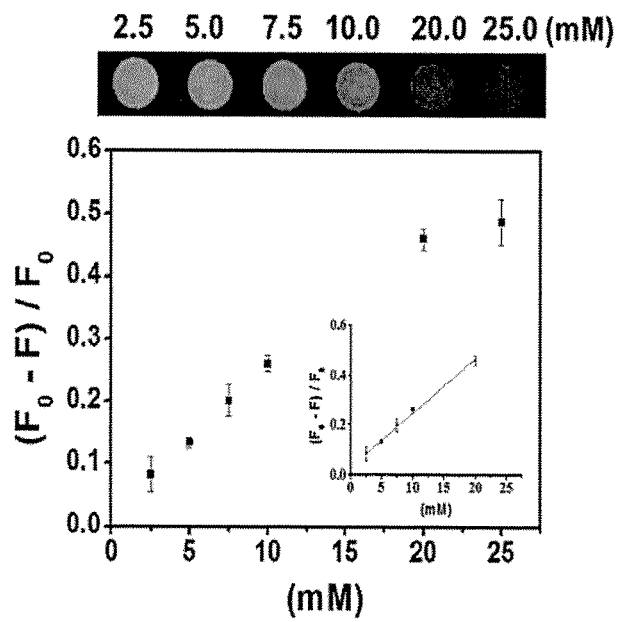
FIG. 5A illustrates a standard concentration versus relative fluorescence quenching rate curve plotted under irradiation of ultraviolet light at 365 nm after the sensing paper reacts with 4-Chloroethcathinone of different concentrations in an embodiment of the invention.
Figure 5B:
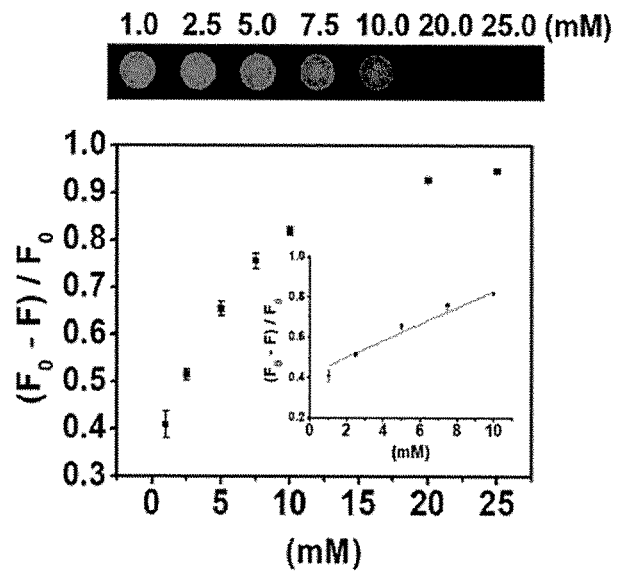
FIG. 5B illustrates a standard concentration versus relative fluorescence quenching rate curve plotted under irradiation of ultraviolet light at 256 nm after the sensing paper reacts with 4-Chloroethcathinone of different concentrations in an embodiment of the invention.

FIG. 5A illustrates a standard concentration versus relative fluorescence quenching rate curve plotted under irradiation of ultraviolet light at 365 nm after the sensing paper reacts with 4-Chloroethcathinone of different concentrations in an embodiment of the invention. As shown in FIG. 5A, as the concentration of 4-Chloroethcathinone becomes higher, the quenching rate of the carbon quantum dots also becomes higher. In other words, the amount of 4-Chloroethcathinone and the quenching rate of the carbon quantum dots are positively correlated, wherein a detection limit of 4-Chloroethcathinone irradiated with ultraviolet light at 365 nm is about 2.00 mM. FIG. 5B illustrates a standard concentration versus relative fluorescence quenching rate curve plotted under irradiation of ultraviolet light at 256 nm after the sensing paper reacts with 4-Chloroethcathinone of different concentrations in an embodiment of the invention. As shown in FIG. 5B, as the concentration of 4-Chloroethcathinone becomes higher, the quenching rate of the carbon quantum dots also becomes higher. In other words, the amount of 4-Chloroethcathinone and the quenching rate of the carbon quantum dots are positively correlated, wherein a detection limit of 4-Chloroethcathinone irradiated with ultraviolet light at 256 nm is about 0.82 mM. As shown by the experimental results above, the sensing result obtained by using the sensing paper is similar to the result obtained in the solution in Experimental Example A. Therefore, it is proven that abused drugs such as 4-Chloroethcathinone may be effectively sensed by using the sensing paper of the invention.

Figure 5C:
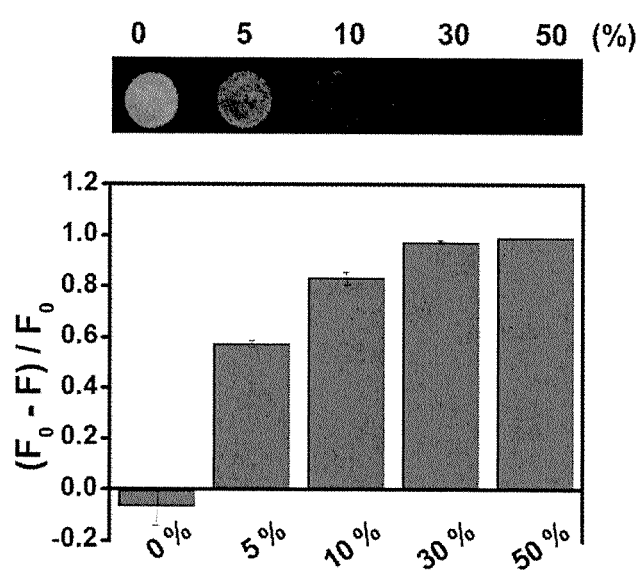
FIG. 5C is a graph illustrating values of the relative fluorescence quenching rates of the sensing paper after reacting with 4-Chloroethcathinone and glucose in an embodiment of the invention.

In addition, due to its white powdery form, glucose is commonly doped in abused drugs. Therefore, the inventors have doped glucose into 5% to 50% by weight of 4-Chloroethcathinone, and dripped this solution on the sensing paper having the carbon quantum dots for sensing. The experimental result is shown in FIG. 5C. FIG. 5C is a graph illustrating values of the relative fluorescence quenching rates of the sensing paper after reacting with 4-Chloroethcathinone and glucose in an embodiment of the invention. Referring to FIG. 5C, it is noted that even under a mixture of 5% concentration of 4-Chloroethcathinone with glucose, the fluorescence intensity can be effectively quenched to a certain extent. In other words, doping of glucose does not affect the fluorescence quenching rate of 4-Chloroethcathinone. Therefore, it is proven that the sensing paper of the invention can be used to accurately and rapidly identify the presence of abused drug in the sensing solution using the naked eye.

Experimental Example D

Figure 6:
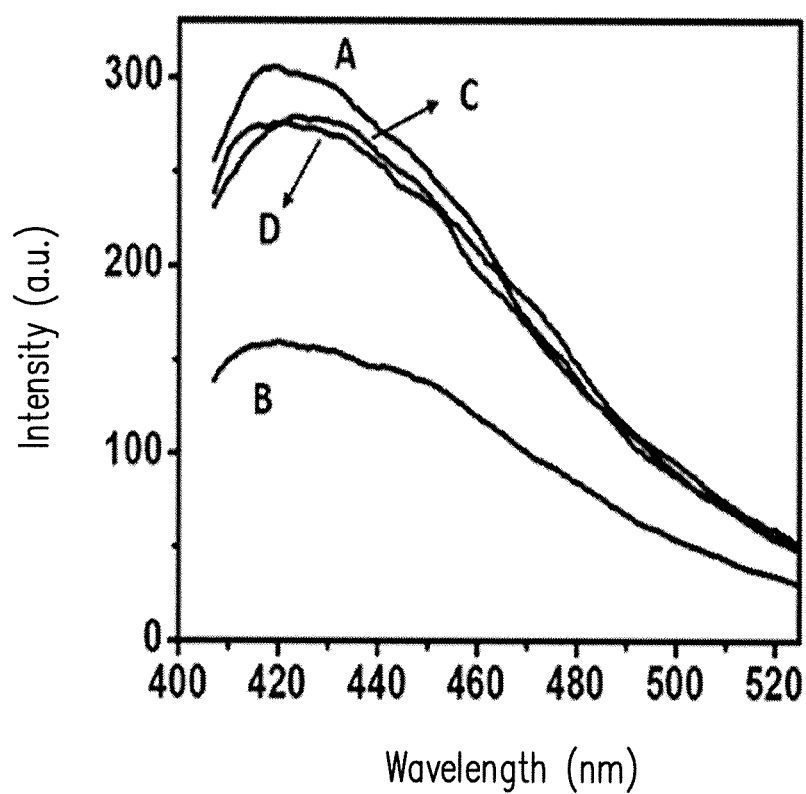
FIG. 6 illustrates fluorescence emission spectra of the carbon quantum dots in the presence and absence of 4-Chloroethcathinone and in the presence and absence of a reducing agent in an embodiment of the invention.

To verify the reaction mechanism of 4-Chloroethcathinone and the carbon quantum dots, 4-Chloroethcathinone and a reducing agent (sodium borohydride, NaBH$_4$) are mixed and reacted and then irradiated with ultraviolet light to verify its fluorescence emission spectrum. The experimental result is shown in FIG. 6. FIG. 6 illustrates fluorescence emission spectra of the carbon quantum dots in the presence and absence of 4-Chloroethcathinone and in the presence and absence of the reducing agent in an embodiment of the invention. Referring to FIG. 6, spectrum A is a fluorescence emission spectrum of the carbon quantum dots detected in the absence of 4-Chloroethcathinone; spectrum B is a fluorescence emission spectrum of the carbon quantum dots detected in the presence of 4-Chloroethcathinone; and spectrum C and spectrum D are fluorescence emission spectra of the carbon quantum dots detected in the presence of 4-Chloroethcathinone and the reducing agent mixed for 20 minutes (C) and 40 minutes (D). The experimental result shows that when 4-Chloroethcathinone is mixed with the reducing agent (sodium borohydride), the fluorescence intensity is similar to the experimental result where 4-Chloroethcathinone is not added. In other words, addition of the reducing agent inhibits 4-Chloroethcathinone from effectively quenching the fluorescence intensity of the carbon quantum dots. Since sodium borohydride reduces the ketone functional group of 4-Chloroethcathinone, it is verified that quenching of the fluorescence intensity of the carbon quantum dots is mainly due to the ketone functional group of 4-Chloroethcathinone.

In summary, as the sensing paper of the invention is attached with the fluorescent materials, when the fluorescent materials react with molecules of the abused drug, the fluorescence of the fluorescent materials is rapidly quenched, and the concentration of the abused drug can be quantified based on the quenching rate. By using the fluorescent materials as the sensing substances, the sensing paper of the invention exhibits advantages including high stability, stability to heat and humidity, resistance to deterioration, and ease of storage. Moreover, quality control of the chemically synthesized fluorescent materials may be monitored, such that high stability is secured among batches of products. In addition, the fluorescent materials of the invention may be synthesized from organic materials, and even organic waste materials can all be used as synthesis precursors of the invention, which is in line with the concept of green chemistry. In other words, the sensing paper of the invention exhibits advantages of manufacturing simplicity, low costs, and ease of storage and is suitable for sensing a variety of abused drugs.

Although the invention is disclosed as the embodiments above, the embodiments are not meant to limit the invention. Any person skilled in the art may make slight modifications and variations without departing from the spirit and scope of the invention. Therefore, the protection scope of the invention shall be defined by the claims attached below.

What is claimed is:

1. A sensing paper suitable for sensing a target substance, the sensing paper comprising:
   a filter paper;
   a wax printed on the filter paper, wherein the wax has a plurality of opening patterns, and the opening patterns respectively expose a portion of the filter paper; and
   a plurality of fluorescent materials attached to the portion of the filter paper that is exposed by the opening patterns, wherein the fluorescent materials emit fluorescence, and after the fluorescent materials react with the target substance, an intensity of the fluorescence emitted by the fluorescent materials is quenched.

2. The sensing paper according to claim 1, wherein the opening patterns are circular opening patterns, and the circular opening patterns are disposed separate from each other.

3. The sensing paper according to claim 1, wherein the wax is printed on a first surface and a second surface opposite to the first surface on the filter paper, and the wax on the first surface has the opening patterns and the wax on the second surface does not have the opening patterns.

4. The sensing paper according to claim 1, wherein the fluorescent materials are carbon quantum dots, and a size of the carbon quantum dots respectively ranges from 2.77 nm to 6.14 nm.

5. The sensing paper according to claim 4, wherein a highest occupied molecular orbital (HOMO) of the carbon quantum dots is −4.51 eV, and a lowest unoccupied molecular orbital (LUMO) of the carbon quantum dots is −1.48 eV.

6. The sensing paper according to claim 1, wherein a lowest unoccupied molecular orbital (LUMO) of the target substance to be sensed is lower than a lowest unoccupied molecular orbital (LUMO) of the fluorescent materials, so that the fluorescent materials undergo electron transfer and cause the intensity of the fluorescence emitted by the fluorescent materials to be quenched.

7. The sensing paper according to claim 1, wherein the fluorescent materials emit blue fluorescence after being excited by ultraviolet light, and after the fluorescent materials react with the target substance, an intensity of the blue fluorescence emitted by the fluorescent materials is quenched.

8. The sensing paper according to claim 1, wherein the target substance is cocaine or cathinone.

9. A method of sensing abused drugs, comprising:
   providing the sensing paper according to claim 1;
   dripping a sensing liquid into at least one of the opening patterns of the sensing paper;
   performing irradiation with an ultraviolet light source after the sensing liquid reacts with the fluorescent materials in the opening pattern; and
   under the irradiation of the ultraviolet light source, determine a quenching rate of the intensity of the fluorescence of the fluorescent materials in the opening pattern so as to verify the presence of an abused drug in the sensing liquid, and verifying a concentration of the abused drug in the sensing liquid according to the quenching rate.

10. The method according to claim 9, wherein 10 μL of the sensing liquid is dripped into the at least one of the opening patterns of the sensing paper for reaction.

11. The method according to claim 9, wherein after the sensing liquid reacts with the fluorescent materials in the opening pattern, a solvent of the sensing liquid is evaporated and then the irradiation is performed with the ultraviolet light source.

12. The method according to claim 9, wherein a method of verifying the concentration of the abused drug in the sensing liquid according to the quenching rate comprises:
   providing a series of the abused drug at known concentrations in the opening patterns of the sensing paper;
   performing irradiation with the ultraviolet light source after the abused drug reacts with the fluorescent materials in the opening patterns;
   determining fluorescence intensities with the abused drug at each concentration to plot a standard concentration versus relative fluorescence quenching rate curve; and determining the quenching rate based on the standard concentration versus relative fluorescence quenching rate curve to verify the concentration of the abused drug in the sensing liquid.

* * * * *